(12) United States Patent
Eastman

(10) Patent No.: US 7,003,345 B1
(45) Date of Patent: Feb. 21, 2006

(54) SYSTEM AND METHOD FOR ENHANCING MICROSCOPE IMAGES OF TISSUE USING CITRIC ACID AND AGENTS OF THE LIKE

(75) Inventor: Jay M. Eastman, Pittsford, NY (US)

(73) Assignee: Lucid, Inc., Rochester, NY (US)

( * ) Notice: Subject to any disclaimer, the term of this patent is extended or adjusted under 35 U.S.C. 154(b) by 0 days.

(21) Appl. No.: 09/978,965

(22) Filed: Oct. 15, 2001

Related U.S. Application Data

(60) Provisional application No. 60/241,092, filed on Oct. 17, 2000.

(51) Int. Cl.
A61B 6/00 (2006.01)
(52) U.S. Cl. .................. 600/431; 600/704; 600/437; 600/458; 600/476; 424/9.1; 424/9.5; 424/9.8
(58) Field of Classification Search ............... 600/407, 600/431, 437, 458, 476; 424/9.3, 9.5, 9.8, 424/9.1
See application file for complete search history.

(56) References Cited

U.S. PATENT DOCUMENTS

| | | | |
|---|---|---|---|
| 4,298,590 A | | 11/1981 | Bogoch |
| 5,034,613 A | | 7/1991 | Denk et al. |
| 5,496,535 A | * | 3/1996 | Kirkland ............... 424/9.37 |
| 5,733,739 A | | 3/1998 | Zakim et al. |
| 5,788,639 A | | 8/1998 | Zavislan et al. |
| 5,880,880 A | | 3/1999 | Anderson et al. |
| 5,995,867 A | | 11/1999 | Zavislan et al. |
| 6,151,127 A | | 11/2000 | Kempe |
| 6,187,289 B1 | | 2/2001 | Richards-Kortum et al. |
| 6,241,662 B1 | * | 6/2001 | Richards-Kortum et al. ........ 600/310 |
| 6,264,914 B1 | | 7/2001 | Klaveness et al. |
| 6,319,488 B1 | | 11/2001 | Licha et al. |
| 6,348,325 B1 | | 2/2002 | Zahniser et al. |
| 6,498,945 B1 | * | 12/2002 | Alfheim et al. ........... 600/407 |

FOREIGN PATENT DOCUMENTS

CN  1192930 A  *  9/1998
WO  00/55669  9/2000

OTHER PUBLICATIONS

Burghardt, E., Colposcopy Cervical Pathology, Textbook and Atlas, Published by Thieme-Stratton Inc., New York (1984), Foreword and pp. 112-120.
Cortext Technology, Research equipment for dermatology, DermaScan C series—high frequency ultrasound units, Printout of Web Site at http://mail.cortex.dk/newct2.htm, pp. 1-3, Jan. 8, 2002.
Fraschini, A. et al., The Effect of Different Fixatives on Chromatin: Cytochemical and Ultrastructural Approaches, Histochemical Journal, vol.. 13, pp. 763-779 (1981).
Rajadhyaksha et al., In Vivo Confocal Scanning Laser Microscopy of Human Skin: Melanin Provides Strong Contrast, The Journal of Investigative Dermatology, vol. 104, No. 6, Jun. 1995, pp. 946-952.
Rajadhyaksha and Zavislan, Confocal laser microscopy images tissue in vivo, Laser Focus World, Feb. 1997, pp. 119-127.
Schmitt et al., Optical characterization of dense tissues using low-coherence Interferometry, Proc. of SPIE, vol. 1889, (1993), pp. 197-211.
Brochure, Looking Through The Window of Life, Lucid VivaScope, Lucid Technologies, Inc.
Cortex Technology, New products for skin analysis, Printout of Web Site at www://mail.cortexdk/ctnewprod.htm, p. 1, Jan. 8, 2002.
Amarante, Skin Care Products from Amarante featuring Alpha Hydroxy Acid, Printout of Web Site at http://www.amaranteskincare.com/, pp. 1-2, Jan. 24, 2002.

* cited by examiner

*Primary Examiner*—Ruth S. Smith
(74) *Attorney, Agent, or Firm*—Kenneth J. Lukacher

(57) ABSTRACT

A system and method for enhancing images of ex-vivo or in-vivo tissue produced by confocal microscopy, optical coherence tomography, two-photon microscopy, or ultrasound, is provided by applying to the tissue a solution or gel having an effective concentration of citric or other alpha-hydroxy acid which enhances tissue structures, such as cellular nuclei, in such images. Such concentration may be 3–20% acid, and preferably 5% acid.

17 Claims, No Drawings

SYSTEM AND METHOD FOR ENHANCING MICROSCOPE IMAGES OF TISSUE USING CITRIC ACID AND AGENTS OF THE LIKE

This application claims the benefit of priority to U.S. Provisional Patent Application No. 60/241,092, filed Oct. 17, 2000, which is herein incorporated by reference.

FIELD OF THE INVENTION

The present invention relates to a system and method for improving the contrast of nuclear structures of in-vivo and ex-vivo tissues for imaging by microscopy and particularly confocal microscopy, and also by optical coherence tomography, two-photon microscopy, and ultrasound.

BACKGROUND OF THE INVENTION

Confocal microscopes for scanning tissue can produce microscopic image sections of tissue. Such microscopic image sections may be made in-vivo in tissue without requiring a biopsy specimen of the lesion. Examples of confocal scanning microscopes are found in Milind Rajadhyaksha et al., "In-vivo Confocal Scanning Laser Microscopy of Human Skin: Melanin provides strong contrast," Journal of Investigative Dermatology, Volume 104, No. 6 Jun. 1995, pages 1–7, and in Milind Rajadhyaksha et al., "Confocal laser microscope images tissue in vivo," Laser Focus World, February 1997 pages 119–127. These systems have confocal optics which direct light to the patient's tissue and image the returned reflected light. Imaging in the confocal microscope may be with illumination at different or multiple wavelengths which may be applied simultaneously. Microscope images of tissue sections can also be produced by optical coherence tomography or interferometry, such as described in Schmitt et al., "Optical characterization of disease tissues using low-coherence interferometry," Proc. Of SPIE, volume 1889 (1993). Another type of imager used to image microscopic section is a two-photon laser microscope, such as described in U.S. Pat. No. 5,034,613 to Denk et al., issued Jul. 23, 1991. Finally, microscopic images sections can be imaged using high-frequency ultra-sound imaging systems such as DermaScanC manufactured by Cortex Technologies of Denmark.

Confocal microscopes and optical coherence tomography systems image native optical refractive index variation within the epithelial and stromal compartments of the tissue. These refractive index variations are due to the chemical variations and structural configurations of the chemical compounds within the tissue. Structures that backscatter more light appear brighter than less scattering structures. In general, whenever there is a large refractive index change between two cellular structures, there is the possibility for a high degree of backscatter. Ultrasound systems image the native sonic refractive index variations within the epithelial and stromal compartments of the tissue. These sonic refractive index variations are related to the density variations in the tissue. Two-photon microscopy images the fluorescence spectra of the tissue components.

Traditional pathological interpretation of cellular images focuses on the identification of cell type and its location and the morphology of the cellular structures for example the nuclear to cytoplasm ratio. Thus, it is important that the images of in-vivo and ex-vivo tissue have contrast sufficient to allow for the visualization of the overall cell size and the geometry of the nucleus.

Depending on the tissue type and its condition, different cellular components image with different contrast. For example, the nuclei of oral mucosal cells image appear bright compared to its cytoplasm, when viewed by near-infrared confocal microscopy. The nuclei of granular cells in the skin image dark compared to the cytoplasm of the skin when viewed by near-infrared confocal microscopy. The difference can be attributed to the difference in refractive index between the cytoplasm and nuclei, and the size and shape of the structures that make up the nucleus and cytoplasm. The nuclei of both oral mucosa and granular cells contain nucleic acids. The cytoplasm of oral mucosal cells is highly aqueous which suspend direct organelles such as mitochondria. The average refractive index of the cytoplasm is thus close to a normal saline solution approximately 1.34. The cytoplasm of granular cells is filled with the keratohyalin granules. The granules have a refractive index approaching 1.5. Their size, which is on the order of a wavelength of light, also facilitates the backscatter of light.

Thus, it is desirable to provide for a method and solution to modify the configuration of the constituents of in-vivo and ex-vivo tissues so as to enhance the visibility of cellular structures, such as the nucleus of the cell, which may use staining agents other than acetic acid solutions as have heretofore been used and is described, for example, in U.S. Pat. No. 5,733,739. Dilute acetic acid is known to "whiten" abnormal epithelium such as dermal papillomas (warts) and cervical lesions, and 5% acetic acid (vinegar) is routinely used in colposcopic examination. 5% acetic acid is also used to localize warts prior to treatment. The acetic acid "whitens" the tissue by condensing the nucleic acids (chromatin) within the nucleus. The condensed chromatin enhances the optical backscatter from the modified nucleus.

SUMMARY OF THE INVENTION

It is an object of the present invention to provide a system and method for enhancing images of tissue using citric or other alpha-hydroxy acid, and particularly images produced by confocal microscopy, optical coherence tomography, two-photon microscopy or ultrasound.

It is another object of the present invention to provide a system and method for enhancing images of tissue using citric or other alpha-hydroxy acid which is applied to tissue in a solution or gel to enhance visibility of tissue structures in images.

Briefly described, the method comprises coating, immersing, rinsing, or diffusing, an in-vivo or ex-vivo tissue specimen in an effective concentration of citric acid prior to or during imaging of the specimen which enhances the contrast of tissue structures, such as nuclei or cells, in images produced by such imaging. Imaging of the tissue may be provided by systems operating in accordance with confocal microscopy, optical coherence tomography, two-photon microscopy or ultrasound. The citric acid may be a solution or gel in water in the concentration of 3–20% citric acid to water, and preferably 5% citric acid to water. Other alpha-hydroxy acids at the same concentrations may be used instead of citric acid.

A system is also provided having an imaging system for producing images of tissue having an effective concentration of citric, or other alpha-hydroxy acid to provide enhancement of tissue structures in such images.

DETAILED DESCRIPTION OF THE INVENTION

Confocal microscopy, such as provided by the VIVASCOPE® confocal microscope sold by Lucid, Inc. of Rochester, N.Y., are capable of imaging in-vivo and ex-vivo tissue to provide microscopic sections of such tissue which may show structures such as cells and their nuclei. Examples of confocal microscopes are described in U.S. Pat. Nos. 5,788,639, 5,995,867, 5,880,880, and 6,151,127. However, in addition to such confocal imaging systems, other imaging systems may be used which are capable of providing sectional images of tissue, including systems operating by optical coherence tomography, two-photon laser microscopy, and ultrasound, as described earlier.

It has been found that citric acid and other alpha-hydroxy acids enhance the visibility of the nucleus in images of tissue. Citric acid may be used in solutions of 3–20% citric acid in water. It may be applied by immersion, dipping, rinsing or enclosing the specimen in a gel. The mechanism of action is not known. The solution may be applied prior to or during imaging of the tissue specimen.

As a specific example, to produce the brightening, the tissue is exposed to the agent for 30 seconds to 3 minutes by rinsing or submerging in a 5% citric acid solution in water. Keratinizing tissue, such as skin, may require preparation, such as tape stripping or abrasion of the upper tissue layers (e.g., the stratum corneum), to facilitate exposure of deeper layers of tissue.

After exposure, the cell nuclei appear brighter in images of tissue which facilitates pathological diagnosis. The exposure of the tissue to the alpha-hydroxy acids, such as citric acid, also improves the contrast of the tissue to other imaging modalities, such as ultrasound, since the increased backscatter may be associated with a change in density of the tissue which in turn will effect the sonic refractive index of the tissue. Additionally, the change in physical configuration of the nucleic acids will shift the fluorescence spectra of the tissue which will in turn affect the contrast of the images produced by two-photon confocal imaging or other fluorescence based imaging. Optical coherence tomography imaging may also experience enhanced contrast of images by exposure to alpha-hydroxy acids.

From the foregoing description, it will be apparent that improved system and method for enhancing images by the use of citric or other alpha hydroxy acids is provided. Variations and modifications in the herein described system and method will undoubtedly become apparent to those skilled in the art. Accordingly, the foregoing description should be taken as illustrative and not in a limiting sense.

What is claimed is:

1. A method for enhancing contrast in images of in-vivo or ex-vivo tissue comprising the steps of:

directly applying to said tissue an image contrast enhancing agent consisting of an effective concentration of alpha-hydroxy acid to enhance contrast of structures in said tissue in which the response of said tissue to said alpha-hydroxy acid in and of itself directly provides said enhancement of contrast of said structures in said tissue; and imaging said tissue.

2. The method according to claim 1 wherein said structures represent nuclei of cells of said tissue.

3. The method according to claim 1 wherein said concentration is 3–20%.

4. The method according to claim 1 wherein said concentration is 5%.

5. The method according to claim 1 wherein said applying step is carried out during said imaging step.

6. The method according to claim 1 wherein said applying step is carried out before said imaging step.

7. The method according to claim 1 wherein said imaging step is carried out by one of confocal microscopy, optical coherence tomography, two-photon microscopy, or ultrasound.

8. The method according to claim 1 wherein said applying step comprises one of coating, immersing, rinsing, or diffusing said alpha-hydroxy acid to said tissue.

9. The method according to claim 1 wherein said tissue represents one of an in-vivo or ex-vivo tissue specimen.

10. The method according to claim 1 wherein said alpha-hydroxy acid represents citric acid.

11. The method according to claim 1 wherein said concentration of said alpha-hydroxy acid is capable of enhancing contrast of nuclei in cells of the imaged tissue.

12. A method of using citric acid to enhance contrast for imaging cells comprising the steps of:

directly applying an image enhancing agent consisting of citric acid to tissue in sufficient concentration whereby the response of said tissue to said citric acid enhances in and of itself contrast of nuclei in the cells; and imaging the tissue having said cells.

13. The method according to claim 12 wherein said imaging is carried out by confocal imaging.

14. The method according to claim 12 wherein said imaging is carried out by optical coherence tomography, two-photon microscopy or ultrasound.

15. The method according to claim 12 wherein said concentration of said citric acid is 3% to 20%.

16. The method according to claim 12 wherein said concentration of said citric acid is 5%.

17. The method according to claim 12 wherein said tissue is one of in-vivo or ex-vivo tissue.

* * * * *